United States Patent [19]

DeWald et al.

[11] Patent Number: 4,960,885

[45] Date of Patent: Oct. 2, 1990

[54] PROCESS FOR PRODUCING METHYLENE BIS(PHENOTHIAZINES)

[75] Inventors: Raymond C. DeWald, Douglassville; Paul O. Hong, Paoli, both of Pa.

[73] Assignee: Occidental Chemical Corporation, Niagara Falls, N.Y.

[21] Appl. No.: 344,169

[22] PCT Filed: Jul. 26, 1988

[86] PCT No.: PCT/US88/02462

§ 371 Date: Feb. 16, 1989

§ 102(e) Date: Feb. 16, 1989

[87] PCT Pub. No.: WO89/00993

PCT Pub. Date: Feb. 9, 1989

Related U.S. Application Data

[63] Continuation-in-part of Ser. No. 79,315, Jul. 30, 1987, Pat. No. 4,855,424.

[51] Int. Cl.⁵ .......................................... C07D 279/20
[52] U.S. Cl. ................................................... 544/35
[58] Field of Search .......................................... 544/35

[56] References Cited

U.S. PATENT DOCUMENTS 4,229,510 10/1980 Watarai et al. .................. 430/38
4,565,834 1/1986 Buysch et al. .................. 544/35 Y

OTHER PUBLICATIONS

Romanovich et al, Chemical Abstracts, vol. 98(1983) 144251d.

*Primary Examiner*—Richard L. Raymond
*Attorney, Agent, or Firm*—James F. Tao; James F. Mudd; Richard D. Fuerle

[57] ABSTRACT

A composition having the formula

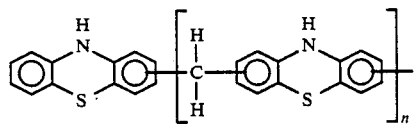

wherein n has an average value of one to about five, is disclosed for use in reducing or eliminating the formation of reactor scale during the polymerization of vinyl chloride and comonomers. The composition is prepared by reacting phenothiazine with formaldehyde in the presence of a liquid diluent that is a solvent for the phenothiazine, but a non-solvent for the dimer of phenothiazine and formaldehyde. The process of the invention is preferably conducted in the presence of a strong acid catalyst. The formaldehyde is preferably added slowly to the reaction mixture over the course of the reaction. The product can be filtered and dried.

10 Claims, No Drawings

PROCESS FOR PRODUCING METHYLENE BIS(PHENOTHIAZINES)

This is a continuation-in-part of application Ser. No. 079,315, filed July 30, 1987, now U.S. Pat. No. 4,855,424.

BACKGROUND OF INVENTION AND INFORMATION DISCLOSURE STATEMENT

1. Field of Invention

In the manufacture of polyvinyl chloride and copolymers of vinyl chloride, the resin tends to adhere to the reactor walls during the polymerization of the vinyl chloride and comonomers. The buildup of scale on the reactor walls interferes with heat transfer, it consumes valuable monomer which is lost to the final product, and it results in the increase in waste product that must be disposed of safely.

2. Prior Art

U.S. Pat. No. 2,415,252 describes the preparation of phenothiazine derivatives by reacting phenothiazine with formaldehyde and an alcohol under conditions that produce a modified phenothiazine that has attached thereto a methylene group and an alkoxy group. The compounds and their solutions in oil are said to be useful for pharmaceutical, veterinary and pest-control purposes.

U.S. Pat. No. 2,528,092 describes the reaction of phenothiazine with formaldehyde and N-dimethylaniline. The resulting compound is useful as an antioxidant for mineral oil lubricants.

U.S. Pat. No. 4,465,881 describes N,N'-dimers of phenothiazine or a substituted phenothiazine. The compounds result from the linkage of two phenothiazine molecules through their N groups. These dimers are prepared by heating phenothiazine in the presence of an organic peroxide. These dimers are disclosed to be useful to stabilize vinyl aromatic compounds such as styrene and substituted styrenes against undesired polymerization.

U.S. Pat. No. 4,529,500 discloses the use of the N,N'-dimer of phenothiazine or a substituted phenothiazine to protect hydrocarbon processing equipment against fouling during the processing of hydrocarbons at elevated temperatures.

An article published in the USSR by Romanovich and co-authors and reported in Chemical Abstracts as 98:144251d, describes the reaction of phenothiazine and formaldehyde under conditions that favor the production of hardened products wherein reaction appears to take place at the nitrogen group of the phenothiazine, ultimately resulting in the formation of cross-linked products of relatively high molecular weight.

In U.S. Pat. No. 4,229,510, a polymer material is formed from a substituted phenothiazine wherein the nitrogen group is substituted with an alkyl group. It appears that reaction with formaldehyde occurs between the phenyl groups and formaldehyde. The resulting product has the nitrogen group blocked with the alkyl group of the starting material. The resulting products are reported to have photoconductive properties.

U.S. Pat. No. 4,565,834 describes compounds that have the formula of a dimer or polymer of phenothiazine. But, nowhere in the description of the patent is disclosed or suggested compounds or polymers wherein the bridging carbon atom has two hydrogen substituents. The patentees compositions are useful as stabilizer-containing reactive components for the production of polyurethane foams which have little or no tendency toward core decolorization.

PURPOSES OF INVENTION

It is a purpose of the present invention to provide a novel composition of matter and process for making the composition.

It is a further purpose of the invention to provide a new composition that functions to prevent or reduce reactor wall fouling or scale deposits, as well as flocculated material, during polymerization of vinyl chloride and comonomers.

Another purpose is to provide a novel polymerization inhibitor.

SUMMARY OF THE INVENTION

In accordance with this invention there are provided novel compounds which have the formula

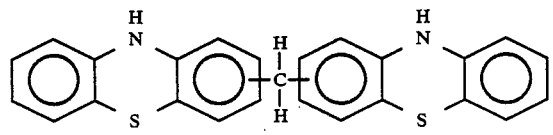

The preferred compound is 3,3'-methylene bis(phenothiazine). The novel compounds are produced by condensing phenothiazine with formaldehyde.

Also provided in accordance with the invention are reaction products comprising the above-mentioned bis(-phenothiazine) compounds and minor amounts of higher condensation products of phenothiazine and formaldehyde.

Further in accordance with the invention there is provided a novel process whereby phenothiazine is reacted with formaldehyde in the presence of a liquid diluent that is a solvent for the phenothiazine, but a non-solvent for the dimer of phenothiazine and formaldehyde and higher oligomers of phenothiazine and formaldehyde.

The process of the invention is preferably conducted in the presence of a strong acid catalyst. The formaldehyde is preferably added slowly to the reaction mixture over the course of the reaction. The product can be filtered and dried.

EMBODIMENTS OF THE INVENTION

The invention involves reaction products of the compound phenothiazine which has the formula

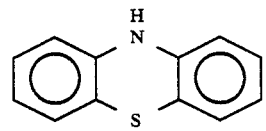

This compound is currently used in animal disease control, in pharmaceutical applications, such as against pinworms in animals.

In the preparation of the compositions of the invention, the phenothiazine is reacted with formaldehyde. The molar ratio of formaldehyde to phenothiazine is generally in the range of about 0.1 to less than 1, preferably in the range of about 0.4 to less than 1, and more preferably about 0.5.

Diluents for the reaction mixture of the invention are liquids that dissolve phenothiazine, but which are not solvents for the dimer of phenothiazine and formaldehyde and higher oligomers of phenothiazine and formaldehyde. Thus, in the course of the reaction, as the dimer and higher oligomers of the phenothiazine are formed, such dimers and higher oligomers precipitate from the diluent and can be removed from the reaction mixture.

Suitable diluents include non-polar solvents such as tetrahydrofuran (THF), dimethylformamide (DMF), cyclohexanone and dimethylsulfoxide (DMSO).

Suitable polar diluents include alcohols, preferably those alcohols having one to five carbon atoms, although higher alcohols up to 10 carbons can be used.

With respect to the reaction of the invention, mixtures of polar and nonpolar solvents are found to be best suited to perform the function of dissolving the monomer but precipitating the dimer and higher oligomers. It is found that the solubility function is important in determining the structure of the product of the invention. Thus, if too powerful a solvent is employed, the dimer and higher oligomers do not precipitate and too high a molecular weight is achieved. If, on the other hand, the solvent is too poor, the monomer has difficulty dissolving and being available for the reaction with the formaldehyde to form the reaction product.

The diluent is employed in the reaction mixture such that the phenothiazine is present in an amount from about one or two weight percent up to about 25 weight percent, preferably up to about 10 weight percent of the diluent. The reaction product should be sufficiently dilute so that it can be filtered to remove the solvent from the product.

The weight ratio of polar to non-polar solvent is generally in the range of about 0.1 to 10, preferably about 0.5 to 2, and still more preferably about 1 to 1.

Either acidic or alkaline compounds can be employed as catalysts for the reaction. However, acid compounds are preferred, and of these the strong acids are more preferred. The preferred compounds include hydrochloric acid, sulfuric acid, nitric acid and phosphoric acid. Suitable caustic compounds include sodium hydroxide and other alkali metal hydroxides.

In the process of the invention, the formaldehyde is slowly added to the mixture of diluent and phenothiazine so that there is an orderly reaction to form the dimer and higher oligomers, and subsequent precipitation of the dimers and oligomers from the reaction mixture.

The preferred reaction temperature is in the range of room temperature to the reflux temperature of the lowest boiling diluent, preferably about 60 to 80 degrees Celsius.

The reaction mixture is removed from the reaction vessel and filtered by conventional means. Suitable filter media include paper and cloth, such as nylon cloth.

The filtered product is dried at a temperature in the range of about room temperature up to the melting point of the composition of the invention, preferably at a temperature of about 50 to 100 degrees Celsius.

The reaction product of the invention generally comprises a mixture of the following components.

| Component | Weight Percent |
| --- | --- |
| Phenothiazine | 1 to 10 |
| Monomer | |
| Dimer | 70 to 85 |
| Trimer | 5 to 15 |
| Higher Oligomers | 5 to 10 |

The reaction product generally has the formula

The reaction product generally has the formula

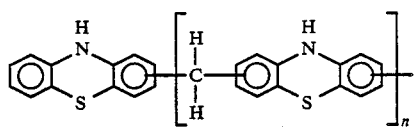

wherein n has an average value of about 1 to about 5, preferably 1 to about 2, and more preferably 1 to about 1.5. The composition is composed of a mixture of individual compounds of the formula wherein n is an integer from 1 to about 10, preferably from 1 to about 5.

The reaction mixture can be processed to change the relative ratios of the foregoing components. Thus, the unreacted monomer can be removed from the reaction mixture by methanol extraction down to about 0.5 weight percent or less of unreacted monomer.

The dimer can be separated from the trimer and higher oligomer materials by a series of extractions with suitable solvents.

The conversion of the phenothiazine to dimer and higher oligomer is generally in the range of about 75 to 90 percent.

The dimer of the invention or the reaction products including the dimer are utilized as follows in the reduction or elimination of scale and flocculated material in a reaction vessel and components such as an agitator used for the polymerization of vinyl chloride. The compositions of the invention are also useful in the polymerization of vinyl chloride with ethylenically unsaturated comonomers in a proportion of up to about 80 mole percent comonomers. Such comonomers include vinyl acetate, and other ethylenically unsaturated monomers that are well known in the art.

The dimer alone or together with higher oligomers is dissolved in a suitable solvent such as THF in a proportion of about 0.3 to about 1 weight percent. The resulting solutions are then brushed or sprayed on the reactor walls, on the reactor agitator, and inside the reactor head. The polymerization reaction mixture is inhibited from forming undesirable scale on the reactor components. Other solvents that can be employed in the application of the solutions to the reactor components include DMF, cyclohexanone and DMSO.

The composition of the invention can also be added directly to the polymerization reaction mixture, generally in a proportion of about 0.0001 to about 0.01 weight percent solids, preferably about 0.001 weight percent solids based on the weight of vinyl chloride and comonomers. The composition of the invention can be added to the polymerization zone as dry solid or in solution in the foregoing solvents. The composition can also be added in the wet cake form after filtering, but before drying in the manufacturing process.

The dimer of the invention or the reaction products including the dimer are also useful in inhibiting the polymerization of monomers such as vinyl chloride or in shortstopping the polymerization of such monomers.

EXAMPLES

In the following examples and throughout the specification and claims, parts are by weight and temperatures are in degrees Celsius, unless indicated otherwise.

EXAMPLE 1

2.0 grams of phenothiazine were dissolved in 8.0 cc of THF. 2.0 cc of concentrated HCl and 1.6 cc of 37 weight percent formaldehyde solution were added to 12.0 cc of methanol. The methanol solution was added slowly with stirring to the THF solution at room temperature. The mixture darkened slightly and became warm. After 5 minutes of stirring, the mixture became cloudy and a precipitate forced. After stirring for 1 hour, the mixture was filtered on a Buchner funnel. The filter cake was slurried with dilute sodium carbonate to remove HCl and again filtered and washed several times with deionized water. After drying for an hour at 60° C., the product was mostly soluble in THF. The soluble portion was tested for reactor buildup control, and analyzed by gel permeation chromatography (GPC) and nuclear magnetic resonance (NMR).

The NMR analysis showed that the major reaction product in the THF soluble portion had the following structure

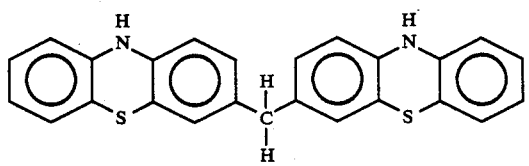

The GPC analysis showed that the soluble portion contained about 80 percent of the dimer of phenothiazine and formaldehyde.

The GPC data coupled with other analyses showed that the solvent-washed product of the invention contained 5 percent phenothiazine, 78 percent dimer, and 17 percent higher oligomers such as trimer, tetramer and higher oligomers.

The soluble portion was found to inhibit reactor fouling during polymerization of vinyl chloride.

EXAMPLE 2

4.0 grams of phenothiazine were dissolved at room temperature with stirring in 8.0 cc of tetrahydrofuran. A solution of 1.0 cc of concentrated hydrochloric acid and 0.4 cc of 37 weight percent formaldehyde solution in 8.0 cc of methanol was added slowly with continued stirring. The solution darkened and after 5 minutes, precipitation began and the mixture rapidly became a thin slurry. At 5-minute intervals, 0.4 cc increments of 37 weight percent formaldehyde solution were added until the mixture contained a total of 2.0 cc of 37 weight percent formaldehyde solution. After 2 hours, the mixture had thickened considerably and 4.0 cc of methanol were added, followed by another 4.0 cc after 3 hours. After 5 hours, the slurry was filtered and washed with a 2/1 mixture by volume of methanol and tetrahydrofuran containing ammonium hydroxide to remove unreacted phenothiazine and to neutralize the hydrochloric acid. The dried product was analyzed by infrared, gel permeation chromatography and nuclear magnetic resonance and found to be 80 weight percent 3,3'-methylene bis(phenothiazine) along with higher oligomers. The infrared analysis showed a strong secondary amine band. The bis(phenothiazine) and higher oligomers are soluble in tetrahydrofuran, dimethylformamide, cyclohexanone and dimethylsulfoxide.

EXAMPLE 3

2.0 grams of phenothiazine, 0.3 grams of paraformaldehyde and 1.0 cc of concentrated hydrochloric acid were added to 18.0 cc of methanol and 4.0 cc of tetrahydrofuran at reflux temperature. Precipitation of product began immediately, and stirring was continued for one-half hour at reflux. The precipitated product was filtered and dried. The dried product was soluble in dimethylformamide. Infrared analysis of the product showed a strong secondary amine band.

EXAMPLE 4

4.0 grams of phenothiazine was dissolved in 10 cc of dimethylformamide. 4.0 cc of concentrated hydrochloric acid and 0.4 cc of 37% formaldehyde solution in 10 cc of methanol were added with stirring. Precipitation began immediately and four more 0.4 cc increments of 37 weight percent formaldehyde solution were added at 2 minute intervals with stirring continued for one-half hour. Solid precipitated product was filtered on paper and was washed with 2/1 parts by volume of methanol/THF solution containing ammonium hydroxide to remove hydrochloric acid and excess phenothiazine. 51 percent yield of dr&ed product was obtained which was soluble in 50/50 parts by volume DMF/THF solution to the extent of 10 weight percent. Infrared analysis of the product showed a strong secondary amine band.

The foregoing examples demonstrate that the desired product is obtained by early precipitation from the reaction medium. The product is prevented from further reacting with formaldehyde to form undesirable, insoluble cross-linked polymer.

EXAMPLE 5

100 grams of phenothiazine were dissolved with stirring in 250 cc of tetrahydrofuran. 46.0 cc of 96 percent sulfuric acid was dissolved in 50 cc of deionized water and cooled, then added slowly with stirring to 250 cc of methanol, followed by 25 cc of 37 weight percent formaldehyde solution. The methanol solution was added slowly with stirring to the tetrahydrofuran solution. The mixture was refluxed for 2 hours with precipitation of product beginning after about 10 minutes. The cooled mixture was neutralized with 40 percent sodium hydroxide solution and then filtered. The filter cake was re-slurried in 750 cc of 50/50 by volume of tetrahydrofuran and methanol. The slurry was stirred 5 minutes and re-filtered. The wet cake was re-slurried and filtered twice in 750 cc portions of 75° C. deionized water. The product was obtained as 32 percent TS wet cake. 80 grams of dried material was obtained from the wet cake. The dried product was soluble in tetrahydrofuran.

EXAMPLE 6 (Control)

4.0 grams of phenothiazine were dissolved in 10 cc of dimethylformamide with stirring and heating to 65° C. Then, 1.0 gram of paraformaldehyde was added, followed by 1.0 cc of concentrated hydrochloric acid. An insoluble gel formed. The solvent was removed. The resulting product was a hard resinous material that was insoluble in dimethyformamide. IR analysis of this product showed no evidence of a secondary amine group. This example showed the importance of controlling reaction conditions in obtaining the desired product, and specifically the effects of higher formaldehyde concentration, high temperature and use of too strong a strong solvent.

EXAMPLE 7

A PVC suspension polymerization process formulated to yield high scale buildup on the reactor walls was carried out at 60° C. in a stainless steel reactor. In the preparation for the polymerization process, the reactor walls, stainless steel agitator and the reactor head were coated with a 0.5 weight percent solution in tetrahydrofuran of product made in accordance with Example 2. The coating was air dried. The following formulation was used:

| Component | Grams |
| --- | --- |
| Vinyl Chloride | 400 |
| Deionized Water | 525 |
| Hydroxypropyl Methylcellulose | 1.10 |
| Partially Hydrolyzed Polyvinyl Acetate | 0.5 |
| 2,2'-azobis (2,4 dimethylvaleronitrile) | 0.10 |

A control polymerization was carried out with the same polymerization formulation, but with no coating employed.

Buildup on all surfaces of the reactor amounted to 40.0 grams for the control polymerization, and 17.0 grams for the coated reactor and components.

EXAMPLE 8

A PVC emulsion polymerization known to yield moderately high reactor buildup was carried out at 50° C. in a glass reactor with a stainless steel agitator. The following polymerization formulation was used:

| | Grams |
| --- | --- |
| Vinyl Chloride | 300 |
| Deionized Water | 600 |
| Potassium Persulfate | 0.2 |
| Sodium Metabisulfite | 0.04 |
| Sodium Bicarbonate | 0.2 |
| Seed Latex (30 weight percent total solids) | 4.8 |
| Sodium Lauryl Sulfate | 2.25* |

*Continuously added over 8 hours in a 3.2 weight percent solution in water.

12.5 ppm (based on the weight of vinyl chloride) of product made in accordance with Example 2 was added to the reactor contents.

A control polymerization was carried out with the same polymerization formulation, but with no product according to Example 2 employed in the process.

In the control reaction, buildup on the metal surfaces and the glass bowl amounted to 5.5 grams together with 10.4 grams of flocculated material. Buildup in the reactor containing the product made in accordance with Example 2 was negligible with 2.5 grams of flocculated material.

EXAMPLE 9

A PVC microsuspension polymerization known to yield high reactor buildup was carried out at 55° C. In preparation for the polymerization process, the agitator was coated with a 2 weight percent solution in tetrahydrofuran of product made in accordance with Example 2. The following polymerization formulation was used:

| | Grams |
| --- | --- |
| Vinyl Chloride | 400 |
| Deionized Water | 370 |
| Sodium Lauryl Sulfate | 4.0 |
| Mixed Fatty Alcohols | 5.0 |
| Lauroyl Peroxide | 0.20 |

In order to provide a high buildup, homogenization of the formulation was carried out for 2½ minutes at low pressure before polymerization.

A control polymerization was carried out with no coating on the agitator.

Buildup on all surfaces of the control reactor amounted to 8.0 grams together with 5.0 grams of flocculated material. Buildup in the reactor with the agitator coated was negligible together with 1.0 grams of flocculated material.

EXAMPLE 10

A PVC mass polymerization was carried out at 50° C. in a glass reactor with a stainless steel agitator with 17 ppm of the product prepared in accordance with Example 1 added to the reactor contents. The following formulation was used:

| Component | Grams |
| --- | --- |
| Vinyl Chloride | 300 |
| Di-Sec.Butyl Peroxydicarbonate | 0.75 |
| Span 60 Surfactant | 1.5 |

100 grams of 0.1% methocel solution was used to wash the Di-Sec.Butyl Peroxydicarbonate and span 60 into the reactor. The reaction was carried out to 28 percent conversion and stopped.

A control polymerization was carried out with no product in accordance with Example 2.

The buildup on the metal surfaces and the glass bowl for the control amounted to 1.25 grams. Buildup in the reactor containing the product from Example 1 was 0.24 grams.

The product of Example 3 prevented buildup and flocculated material in the same fashion as product material from Example 2. Product from Control Example 6 was insoluble in solvents such as THF, and was completely unsuitable for coating reactor components.

EXAMPLE 11

A PVC suspension polymerization process formulated to yield high scale buildup on the reactor walls was carried out at 60° C. in a stainless steel reactor. In preparation for the polymerization process, the reactor walls, stainless steel agitator and the reactor head were coated with 0.5 weight percent solution in tetrahydrofuran of product made in accordance with Example 5, using sulfuric acid as the catalyst. The coating was air dried.

The following formulation was used:

| Components | Grams |
| --- | --- |
| Vinyl Chloride | 400 |
| Deionized Water | 525 |
| Hydroxypropyl Methylcellulose | 1.10 |
| Partially Hydrolyzed Polyvinyl Acetate | 0.50 |
| 2,2'-Azobis (2,4-dimethylvaleronitrile) | 0.10 |

A control polymerization was carried out with the same polymerization formulation but with no coating employed. Buildup on all surfaces of the reactor amounted to 40.0 grams for the control polymerization with no coating, and 9.0 grams for the coated reactor and components.

EXAMPLE 12

The effect of phenothiazine/formaldehyde condensation product prepared in accordance with Example 1 on stopping conversion of vinyl chloride monomer to polymer was examined by carrying out polymerization as described in Example 8. After 6 hours at reaction temperature, 0.06 PHM of condensation product prepared in accordance with Example 1 was added as 10 weight percent solution in 50/50 ratio by volume of DMF/THF. The batch was vented after 18 hours, then cooled, and the percent conversion of monomer to polymer was determined.

EXAMPLE 13

A control polymerization with the addition of 0.06 PHM of Bisphenol A, a known polymerization inhibitor, was carried out in the same way as Example 12.

EXAMPLE 14

A control polymerization with no polymerization inhibitor added was carried out in the same way as Example 12.

Table I compares the effects on monomer conversion of procedures used in Examples 12, 13 and 14.

TABLE I

| MONOMER CONVERSION IN 18 HOURS | |
|---|---|
| Example 12 | 28% |
| Example 13 | 52.5% |
| Example 14 | 76% |

We claim:

1. A process for producing a dimer of phenothiazine and formaldehyde in a diluent comprising reacting about 1 to about 25 weight percent phenothiazine, based on the weight of said diluent, with formaldehyde in a molar ratio to said phenothiazine of about 0.1 to less than 1 in the presence of a liquid diluent that is a solvent for the phenothiazine, but a non-solvent for said dimer, said diluent comprising a mixture of a polar solvent and a non-polar solvent in a weight ratio in the range of about 0.1 to 10.

2. The process of claim 1 conducted in the presence of a strong acid.

3. The process of claim 1 wherein the strong acid is hydrochloric acid or sulfuric acid.

4. The process of claim 1 wherein the diluent is a mixture of tetrahydrofuran and an alcohol.

5. The process of claim 4 wherein the alcohol is methanol.

6. The process of claim 1 wherein the diluent is a mixture of dimethylformamide and an alcohol.

7. The process of claim 6 wherein the alcohol is methanol.

8. The process of claim 1 wherein the formaldehyde is an aqueous solution.

9. The process of claim 1 wherein the formaldehyde is added slowly to the reaction mixture of the phenothiazine and diluent.

10. A process for producing the composition having the following formula

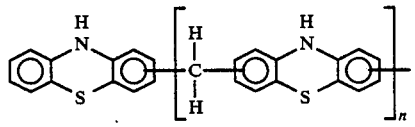

wherein n has an average value of about one to about two, which comprises reacting in a diluent about 1 to about 25 weight percent phenothiazine, based on the weight of said diluent, with formaldehyde in a molar ratio to said phenothiazine of about 0.1 to less than 1, where said diluent is an acidic mixture of methanol and tetrahydrofuran and in a weight ratio in the range of about 0.1 to 10, wherein an aqueous solution of formaldehyde is added slowly to the reaction mixture of phenothiazine and said diluent.

* * * * *